United States Patent
Hippensteel

(10) Patent No.: US 6,835,181 B2
(45) Date of Patent: Dec. 28, 2004

(54) ORAL HYGIENE APPARATUSES USING FAUCET WATER FLOW TO PRODUCE SPRAY JET

(75) Inventor: Joseph B. Hippensteel, 1109 S. Plaza Way #314, Flagstaff, AZ (US) 86001

(73) Assignee: Joseph B. Hippensteel, Flagstaff, AZ (US)

( * ) Notice: Subject to any disclaimer, the term of this patent is extended or adjusted under 35 U.S.C. 154(b) by 253 days.

(21) Appl. No.: 10/112,560

(22) Filed: Mar. 29, 2002

(65) Prior Publication Data

US 2002/0142262 A1 Oct. 3, 2002

Related U.S. Application Data

(60) Provisional application No. 60/280,635, filed on Mar. 30, 2001.

(51) Int. Cl.[7] ............................ A61H 13/00; A61C 3/02
(52) U.S. Cl. ..................... 601/165; 601/162; 604/85; 604/275; 433/88
(58) Field of Search ................... 601/154, 155, 601/159, 160, 161, 162, 163, 165, 169; 433/80, 87, 88, 89; 604/33, 85, 149, 275; 239/310

(56) References Cited

U.S. PATENT DOCUMENTS

| | | | |
|---|---|---|---|
| 3,227,380 A | * | 1/1966 | Pinkston .................... 239/427 |
| 3,971,136 A | * | 7/1976 | Madsen ...................... 433/88 |
| 4,031,908 A | | 6/1977 | Ting |
| 4,043,337 A | | 8/1977 | Baugher |
| 4,106,501 A | | 8/1978 | Ozbey et al. |
| 4,214,871 A | | 7/1980 | Arnold |
| 4,258,734 A | | 3/1981 | Hehlo |
| 4,267,856 A | | 5/1981 | Kwok et al. |
| 4,284,078 A | | 8/1981 | Pace |
| 4,319,595 A | | 3/1982 | Ulrich |
| 4,350,158 A | | 9/1982 | Hudson |
| 4,489,750 A | | 12/1984 | Nehring |
| 4,557,261 A | * | 12/1985 | Rugheimer ................. 604/533 |
| 4,650,470 A | | 3/1987 | Epstein |
| 4,655,197 A | | 4/1987 | Atkinson |
| 4,783,871 A | | 11/1988 | Rich, Jr. |
| 4,903,687 A | | 2/1990 | Lih-Sheng |
| 4,941,459 A | | 7/1990 | Mathur |
| 4,942,870 A | | 7/1990 | Damien |
| 4,958,629 A | | 9/1990 | Peace et al. |
| 5,013,241 A | | 5/1991 | von Gutfeld et al. |
| 5,027,798 A | | 7/1991 | Primiano |
| 5,095,893 A | | 3/1992 | Rawden, Jr. |
| 5,120,219 A | | 6/1992 | De Farcy |
| 5,220,914 A | * | 6/1993 | Thompson .................. 601/155 |
| 5,365,624 A | | 11/1994 | Berns |
| 5,385,533 A | | 1/1995 | Coviello |
| 5,387,182 A | | 2/1995 | Otani |
| 5,500,973 A | | 3/1996 | Phelan |
| 5,547,166 A | * | 8/1996 | Engdahl ..................... 285/313 |
| 5,772,616 A | | 6/1998 | Competiello et al. |
| 5,934,902 A | | 8/1999 | Abahusayn |
| 6,264,119 B1 | | 7/2001 | Truong |
| 6,540,263 B1 | * | 4/2003 | Sausner ...................... 285/305 |
| 6,595,968 B1 | * | 7/2003 | Perrino ....................... 604/279 |

* cited by examiner

Primary Examiner—Nicholas D. Lucchesi
Assistant Examiner—Quang D. Thanh
(74) Attorney, Agent, or Firm—Alston & Bird LLP

(57) ABSTRACT

The disclosed apparatus comprises a valve, a container, first and second coupling devices, a hose, and a jet tip. The valve directs water flow from the faucet to the first coupling device that releasably locks the valve in communication with the container. The water flow travels into the container to mix with oral hygiene substance to produce a liquid mixture. The second coupling device releasably locks the container in communication with the hose to receive and channel the liquid mixture to the jet tip at the hose's opposite end for generation of a spray jet useful in oral hygiene.

20 Claims, 7 Drawing Sheets

ORAL HYGIENE APPARATUSES USING FAUCET WATER FLOW TO PRODUCE SPRAY JET

CROSS-REFERENCE TO RELATED APPLICATIONS

This patent application claims priority under Title 35, United States Code Section 119(e) to U.S. Provisional Patent Application No. 60/280,635 entitled "Dental Water Pik Apparatus Powered by Faucet Water" filed on Mar. 30, 2001, which is incorporated in its entirety by reference and made a part hereof.

FIELD OF THE INVENTION

The present invention relates generally to oral hygiene apparatuses that produce a relatively high-velocity water jet to clean a person's teeth. The apparatuses can be attached to a faucet to receive a flow of water therefrom. The apparatuses use the faucet water flow to produce the jet stream used to clean a person's teeth and gums.

BACKGROUND INFORMATION

U.S. Pat. No. 4,650,470 discloses a water-jet system for use in oral hygiene among other purposes. The system has a diverter valve attached to a faucet, a container, a flow control valve, and a jet adaptor. The container has a wedged nozzle for joining to the diverter valve, a tapered nozzle connector at the end of the hose for coupling to the container, and a wedged nozzle for joining the jet adaptor to the flow control valve. Although this system has certain advantages in being able to mix an oral hygiene solution with water to be sprayed from the jet adaptor for use in oral hygiene, it also has disadvantages that limit its usefulness in many applications. The use of wedged or tapered nozzles provides the possibility that one or more elements will separate if inadvertently contacted. If the system is in use at the time this occurs, a substantial amount of cleaning of the user's clothing or person as well as the area affected by spraying or spillage of water and solution may be required. It would be desirable to overcome these disadvantages of previous devices.

Another disadvantage of previous systems is that if the container is to be refilled with oral hygiene solution, the container must be entirely separated from the system before it can be filled with additional solution or replaced with another container with a different solution. In many oral hygiene apparatuses of this nature, removal and reattachment of the container from the system can be cumbersome and requires a significant amount of time to complete the operation. It would be desirable to overcome these disadvantages of previous oral hygiene apparatuses.

SUMMARY OF THE INVENTION

In their various embodiments, the disclosed apparatuses overcome the disadvantages noted above with respect to previous technologies.

The disclosed oral hygiene apparatus can be used with a faucet providing a flow of water. The apparatus can also be used with an oral hygiene substance. Such substance can be mouthwash, fluoride or other oral treatment, sodium bicarbonate or other relatively soft fine or powdered material that has a hardness less than that of teeth to avoid their damage, and/or toothpaste, for example.

The apparatus comprises a valve, a container, first and second coupling devices, a hose, and a jet tip. The valve is adapted to fit to the faucet to receive a flow of water therefrom. The valve is controllable to selectively provide the water flow through a first faucet orifice and a second auxiliary orifice. The container is used to hold the oral hygiene substance. The first coupling device releasably locks the valve in communication with the container so that the water flow can travel from the second orifice of the valve to the container. The water mixes with the oral hygiene substance in the container to produce a liquid mixture. The second coupling device releasably locks the container in communication with the hose. The second coupling device receives a flow of the liquid mixture from the container and supplies the liquid mixture flow to a first end of the hose. The liquid mixture travels from the first end through the hose to its opposite second end. The jet tip is coupled to receive the liquid mixture from the second end of the hose. The jet tip generates a spray jet with the liquid mixture flow for use in oral hygiene. For example, the spray jet can be used to clean the teeth and gums, to treat the teeth to strengthen them, to improve the appearance of teeth, and/or to freshen breath.

The container can comprise a cap portion and a containment portion. The cap portion can be removably secured to the containment portion to enclose the oral hygiene substance to prevent its escape from the container. The first and second coupling devices can be coupled to the cap portion, a configuration that permits the containment portion to be freely separated from the cap portion to load the container with the oral hygiene substance. The operation of refilling or changing the substance in the container, or replacing the container with a different container holding a different substance, for example, can be carried out relatively easily with the disclosed apparatus.

The first coupling device can comprise opposing spring-loaded levers operable to selectively couple and lock the valve and container in communication with one another, or alternatively, to release the valve and container from communication with one another. In a disclosed configuration of the first coupling device, the first coupling device can have a threaded end that can be screwed into an outlet member defining the second auxiliary orifice of the valve to secure the first coupling device and valve together. The first coupling device can comprise opposing spring-loaded levers for locking the first coupling device in communication with an inlet member of the container.

The second coupling device can comprise opposing spring-loaded levers operable to selectively couple the container and hose in communication with one another, or alternatively, to release the container and hose from communication with one another. The second coupling device can have a threaded end that can be screwed into an outlet member of the container to couple the second coupling device and the container together. The second coupling device can have opposing spring-loaded levers for locking the second coupling device in communication with a coupler of the hose.

The jet tip can define a passage with a relatively wide aperture at its base end tapering to a relatively narrow aperture at its opposite tip end. The base end with the relatively wide aperture can be coupled in communication with the hose to receive the liquid mixture therefrom. The liquid mixture flowing into the base end and through the jet tip's passage is emitted from the relatively narrow aperture at the opposite end of the jet tip in a relatively high-velocity spray jet as compared to the velocity of the liquid mixture flow into the base end of the jet tip due to the tapering of its passage.

A coupling device can be used to couple respective passages of first and second elements in communication with one another. For example, the first element can be the outlet member of a valve or container, and the second element can be the inlet member or inlet portion of a container or hose coupler. The coupling device comprises an inner cylinder, an outer cylinder, first and second pairs of spaced plates, first and second levers, first and second pins, and first and second springs. The inner cylinder defines a passage. The outer cylinder surrounds a first portion of the inner cylinder. The outer cylinder has a closed wall defining an aperture through which a second portion of the inner cylinder extends. The second portion of the inner cylinder has threads defined on an outer surface thereof. The threads of the inner cylinder join with threads defined in an inner surface defining the passage of the first element so that the passage of the inner cylinder communicates with the passage of the first element. The first and second pairs of spaced plates are positioned on opposite sides of the outer cylinder. The first and second levers are positioned between respective first and second pairs of plates. The first and second pins extend through respective first and second levers and have ends supported by the first and second pairs of plates. The first and second levers are pivotally mounted to the first and second pairs of plates by respective first and second pins. The first and second springs have respective first ends fixed to respective first and second levers, and second ends fixed to the outer surface of the outer cylinder. The first and second springs bias respective first and second levers so that the locking ends thereof extend into apertures defined in the outer surface of the outer cylinder to engage with an annular groove of the second element that is positioned between the inner and outer cylinders so that the passage of the second element communicates with the passage of the inner cylinder. The first and second elements thereby are capable of being releasably locked together by the coupling device so that their respective passages communicate with one another. The first and second springs can have respective first and second ends fixed to respective posts defined in the first and second levers and the outer surface of the outer cylinder to prevent the springs from separating from respective first and second levers and the outer surface of the outer cylinder.

Details of the construction and operation of the invention are more fully hereinafter described and claimed. In the detailed description, reference is made to the accompanying drawings, forming a part of this disclosure, in which like numerals refer to like parts throughout the several views.

DESCRIPTION OF THE PREFERRED EMBODIMENTS

Definitions

"And/or" means either or both of the things preceding and succeeding the term.

"Coupled" refers to joining of two parts of the disclosed apparatus, whether directly or indirectly through one or more intermediate elements and/or coupling mechanisms.

"Coupled in communication" means that two parts are joined so that passages defined by the parts are contiguously defined to permit the flow of water or liquid mixture from one part to the other part.

General System and Method

Figure 1:
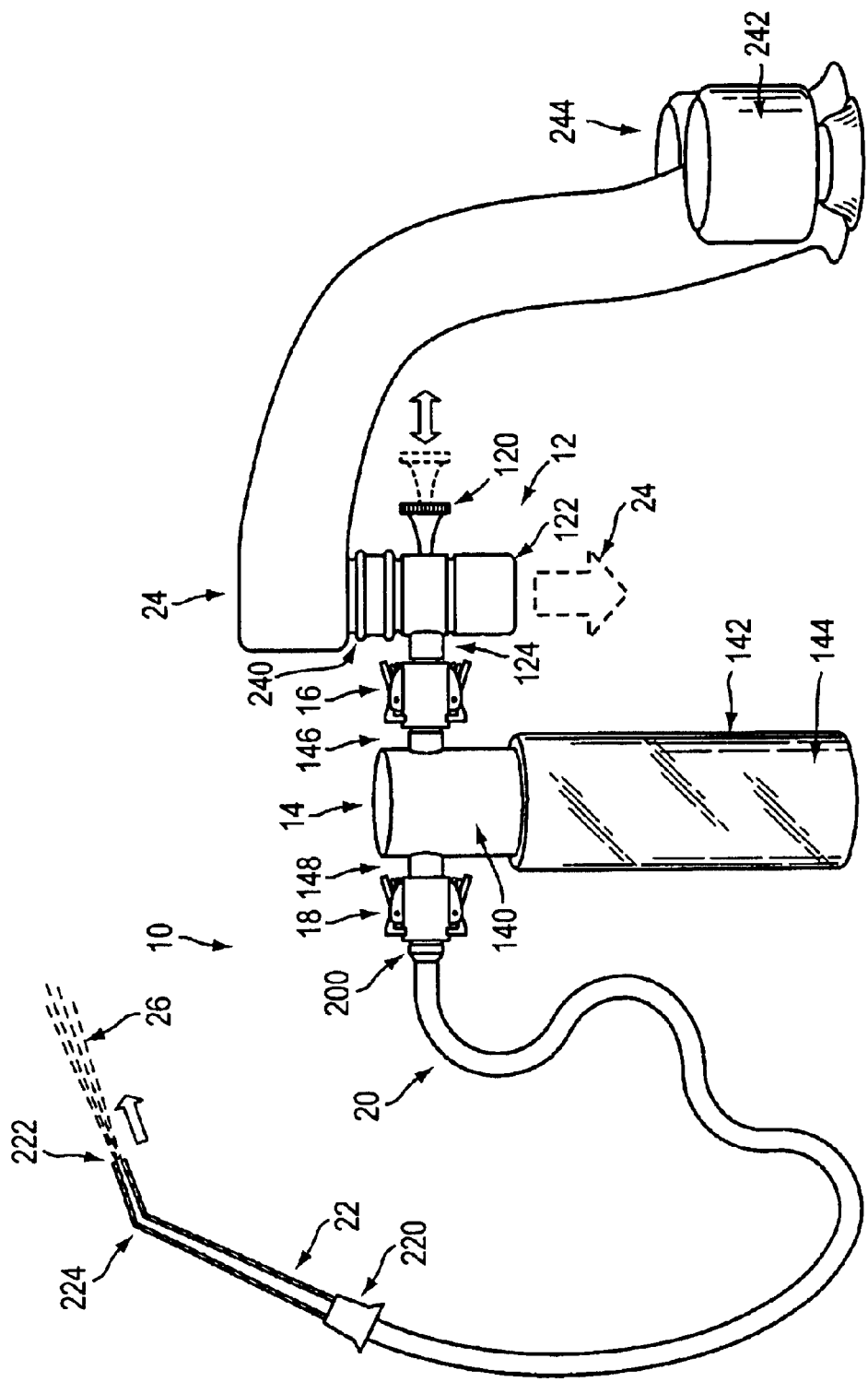
FIG. 1 is a view of a oral hygiene apparatus of the invention comprising diverter valve, container, coupling devices, a hose, and jet tip.

In FIG. 1 the apparatus 10 comprises a diverter valve 12, a container 14, coupling devices 16, 18, a hose 20, and a jet tip 22. The diverter valve 12 is coupled to faucet 24 and receives a flow of water therefrom. The faucet 24 defines a threaded spout 240 to which the diverter valve 12 is threaded. Extending outwardly from its main body, the diverter valve 12 has a stem 120 that is normally biased at a first position that couples internal passages of the diverter valve together in communication to channel water flow from the faucet through the valve to exit at the valve's main orifice 122 in a flow of water 24. The stem 120 can be moved outwardly to a second position that changes the coupling of internal passages within the diverter valve to cause the water flow to be diverted to exit the valve 12 at the outlet member 124. The coupling device 16 is coupled in communication with the diverter valve 12 and the container 14 so that water can flow from the diverter valve to the container 14. More specifically, the outlet member 124 is coupled to inlet member 146 of the container's cap 140 to permit transfer of water from the valve to the container.

The container 14 comprises cap portion 140 and containment portion 142. The cap portion 140 can be screwed onto threads in the neck (not shown in FIG. 1) of the containment portion 142. The containment portion 142 can contain oral hygiene substance 144. The substance 144 can comprise a mouthwash such as those sold under the SCOPE® or LISTERINE® trademarks. As another option, the substance 144 can comprise fluoride or other oral treatment. As yet another option, the substance 144 can comprise sodium bicarbonate or other relatively soft fine or powdered material that has a hardness less than that of teeth to avoid their damage. Such material should be capable of being carried in a stream of water, preferably in undissolved or partially dissolved form to enhance its ability to clean teeth. Furthermore, the substance 144 can comprise a water-thinned toothpaste, for example. Such thinning renders the toothpaste less viscous to avoid blockage of internal passages of the apparatus 10.

The substance 144 mixes with water from the inlet member 146 to form a mixture that flows out from the container 14 through the outlet member 148. The liquid mixture flows from the container 14 through the coupling device 18 to the hose 20. The coupling device 18 is thus coupled in communication with the container 14 and the hose 20 to permit flow of the liquid mixture from the container to the hose. The hose 20 comprises a coupler 200 terminating one end of the hose, that permits the hose 20 to be coupled in communication with the coupler 18. The liquid mixture can thus flow from the container 14 through the coupling device 18 and the coupler 200 into the hose 20. The liquid mixture travels through the hose 20 to its opposite end. This end of the hose 20 is force-fitted over an end of the jet tip 22 to abut with the jet tip's grip 220 so that the hollow interior of the hose communicates with the hollow interior of the jet tip. The jet tip 22 is angled at bend 224 and has an interior passage that is relatively wide where it couples to the hose 20, and that is relatively narrow at aperture 222 at the opposite end of the jet tip 22. Due to the fact that the aperture 222 defined in the jet tip 22 is relatively narrow as compared to its opposite grip end at which the hose is attached, the velocity of the liquid mixture entering the jet tip at the grip end significantly increases in velocity as it moves through the jet tip to the relatively narrow aperture 222 at the end of the jet tip. Spray jet 26 emitted by the jet tip 22 thus has a relatively high-velocity for forceful action to clean away debris or other accumulation such as tartar, plaque or the like from the teeth and gums of the user. The angle or bend 224 of the jet tip 22 provides a configuration that is relatively ergonomic in that it allows the user to grip the jet tip at grip 220 in a natural manner while the angling of the jet tip at bend 224 permits the jet tip to be used to direct the spray jet directly against the teeth and gums for cleaning.

The diverter valve 12 can be comprised of an assembly of metal, metal alloy and/or plastic parts. The container 14, coupling devices 16, 18, coupler 20, and jet tip 22 can be comprised of metal, metal alloy, plastic and/or other materials. The hose 20 can be composed of flexible plastic or rubber tubing, for example.

The temperature of the water used to generate the spray jet 26 can be controlled in the normal manner using hot and cold water controls 242, 244 of faucet 24 to control the proportion of hot and cold water in the water flow. This makes the spray jet 26 comfortable in use against teeth and gums, which can relatively sensitive to temperatures significantly different from body temperature.

Figure 2:
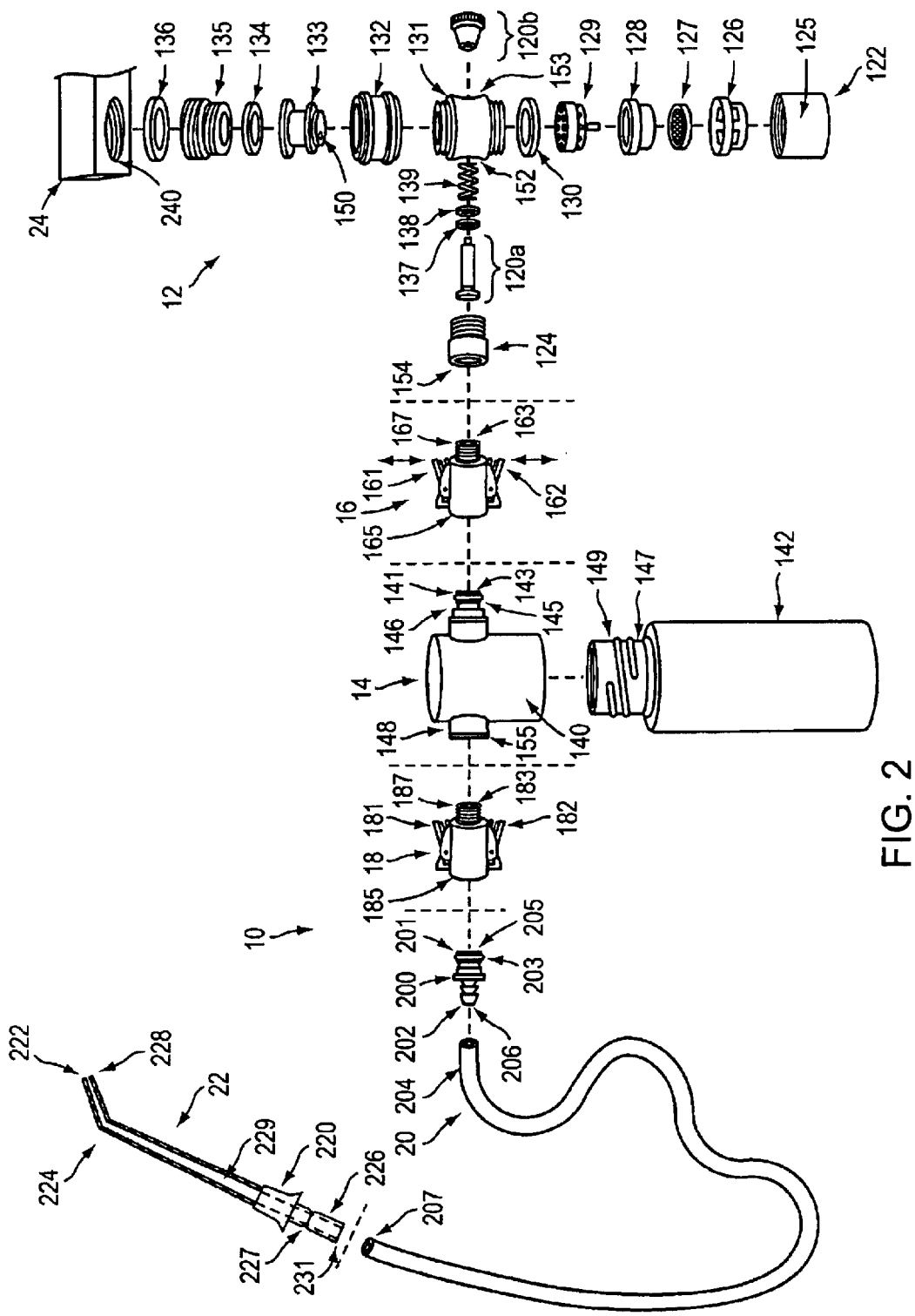
FIG. 2 is an exploded view of the oral hygiene apparatus of the invention.

Referring now to FIG. 2, diverter valve 12 comprises an assembly of several parts. These parts include lower casing 125, screen retainer 126, screen 127, diffuser retainer 128, diffuser 129, resilient washer 130, body 131, collar 132, passage definer 133, O-ring 134, threaded extension 135, resilient washer 136, valve stem parts 120a, 120b, O-ring 137, rigid washer 138, and spring 139. These parts are assembled together in the following manner. The lower casing 125 is cylinder-like with a tapered configuration that is relatively wide at the top and relatively narrow at the bottom defining the main orifice 122. The casing 125 receives and holds the screen retainer 126 at its lower end. A screen 127 is inserted into the retainer 126 which has an annular lower ledge that supports the screen. The diffuser retainer 128 fits inside the screen retainer 126 and is supported by an annular ledge defined therein. The diffuser retainer 128 receives and holds the diffuser 129. The diffuser 129 defines multiple passages to diffuse the water flow received on one side into a relatively large number of smaller water flows. Resilient washer 130 is composed of rubber or other resilient material. The lower casing 122 with encased parts 126, 127, 128, 129, 130 has threads which are joined with corresponding threads defined at the lower end of body 131. The collar 132 is screwed onto the body 131 on a side thereof that is opposite the casing 125 and parts 126–130. The passage definer 133 is driven into the body 131 so that the aperture 150 is located near bore 152 defined in the main body 131. As so positioned, the aperture 150 is positioned in close proximity to the end of the valve stem part 120a. The O-ring 134 fits on the end of the passage definer 133 and the extension 135 is threaded into corresponding threads of the collar 132 to engage with and compress the O-ring 134 between a rim at the top of the passage definer 133 and the end of the extension 135 to form a water-tight fit that permits water to travel only through the interior of the extension 135 and passage definer 133. The resilient washer 136 composed of rubber or the like, is placed on the top edge of the extension 135 and threaded to the spout 240 of the faucet 24 to form a water-tight seal therebetween.

The valve assembly includes a valve stem part 120a over which the O-ring 137 is slid. The O-ring 137 is composed of resilient rubber or plastic material. Valve stem part 120a has a relatively wide end and narrow shaft integrally formed therewith. The rigid washer 138 is then fitted over the valve stem 120a so that the O-ring 137 is retained by the relatively wide end of the part 120a on one side, and the washer 138 on the other side. The O-ring 137 functions to obstruct one passage or another within the body 131, depending upon the position of the valve assembly, to channel water either through the main orifice 122 defined by the lower casing 122 or through side orifice 154 defined by the outlet member 124. The part 120a is further inserted through the spring 139, into the bore 152 defined in the body 131, and out of the bore 153 defined on the opposite side of such body. The end of the part 120a defines threads that mate with corresponding threads inside a hole in the part 120b. To complete the diverter valve assembly, the outlet member 124 is threaded into corresponding threads defined by the body 131 at the bore 152. The outer end of the outlet member 154 defines a hollow interior that is threaded to receive corresponding threads at the end of the coupling device 16. The opposite end of the coupling device 16 can be attached to the outlet member of the cap portion 140 by applying finger pressure to the spring-loaded levers 161, 162 to squeeze them together, sliding the hollow end 165 of the device 16 over the inlet member 146 of the cap portion 140, and releasing the levers 161, 162. The locking ends of the levers 161, 162 are thus positioned in annular groove portion 145 of the inlet member 146 to releasably lock the coupling device 16 to the cap portion 140. As so attached, an interior passage in the coupling device 16 extending from the aperture 163 to the aperture 165 communicates with the interior of the container 14 by a passage extending from aperture 143 through the inlet member. To ensure water-tight engagement of the coupling device 16 to the inlet member 146, the inlet member has an O-ring 141 that engages with the inner surfaces of coupling device 16 and the outer surface of the inlet member 146. The inlet member 146 extends inside of the cap portion 140 and communicates with the interior thereof.

The cap portion 140 can be joined to the containment portion 142 via threads 149 defined in the neck 147 of the containment portion and corresponding threads defined in the inner surfaces of the cap portion 140. The outlet member 148 communicates with the interior of the cap portion 140 and defines a threaded aperture 155. An end 187 of the coupling device 18 is threaded and can be joined with corresponding threads defined in the aperture 155 of the outlet member 148. The opposite end of the coupling device 18 can be joined to the coupler 200 in a manner similar to that previously described with respective to the coupling device 16 and the inlet member 146. In this case, however, rather than forming the annular ring 141 with an O-ring, the coupler 200 can be an integral device molded from plastic, for example, that is provided with an annular ridge 203 extending around the circumference of the end 201 of the coupler 200. This annular ridge 203 forms a water-tight seal between the coupler 18 and the coupler 200 upon joining these components together. The end 202 of the coupler 200 has a series of frusto-conical surfaces that can be inserted into the end 204 of the hose 20. The frusto-conical surfaces engage with the inner surfaces of the hose 20 to from a water tight seal between the coupler and the hose. The coupler 200 defines an internal passage extending from aperture 205 to aperture 206 so that the liquid mixture supplied through the coupler 18 passes through the coupler 200 into the hose 20. The hose 20 guides liquid mixture to the hose's opposite end 207. The opposite end 207 force-fits over the base end 226 of the jet tip 22 to abut with the grip 220. The circumferential groove 227 defined in the jet tip 22 affords additional friction of the hose 20 to the base end 226 so that these elements cannot be readily pulled apart. The jet tip 22 defines a passage 229 extension from the aperture at base end 226 to the aperture 222 at tip end 228. The jet tip 22 can thus channel liquid mixture form the hose 20 through the passage 229 through the aperture 222 at the tip end 228. The passage 229 is defined so as to narrow along the extent of the jet tip 22 from the base end 226 to the end 228 so that the velocity of the flow increases and renders a forceful spray jet 26.

Figure 3:
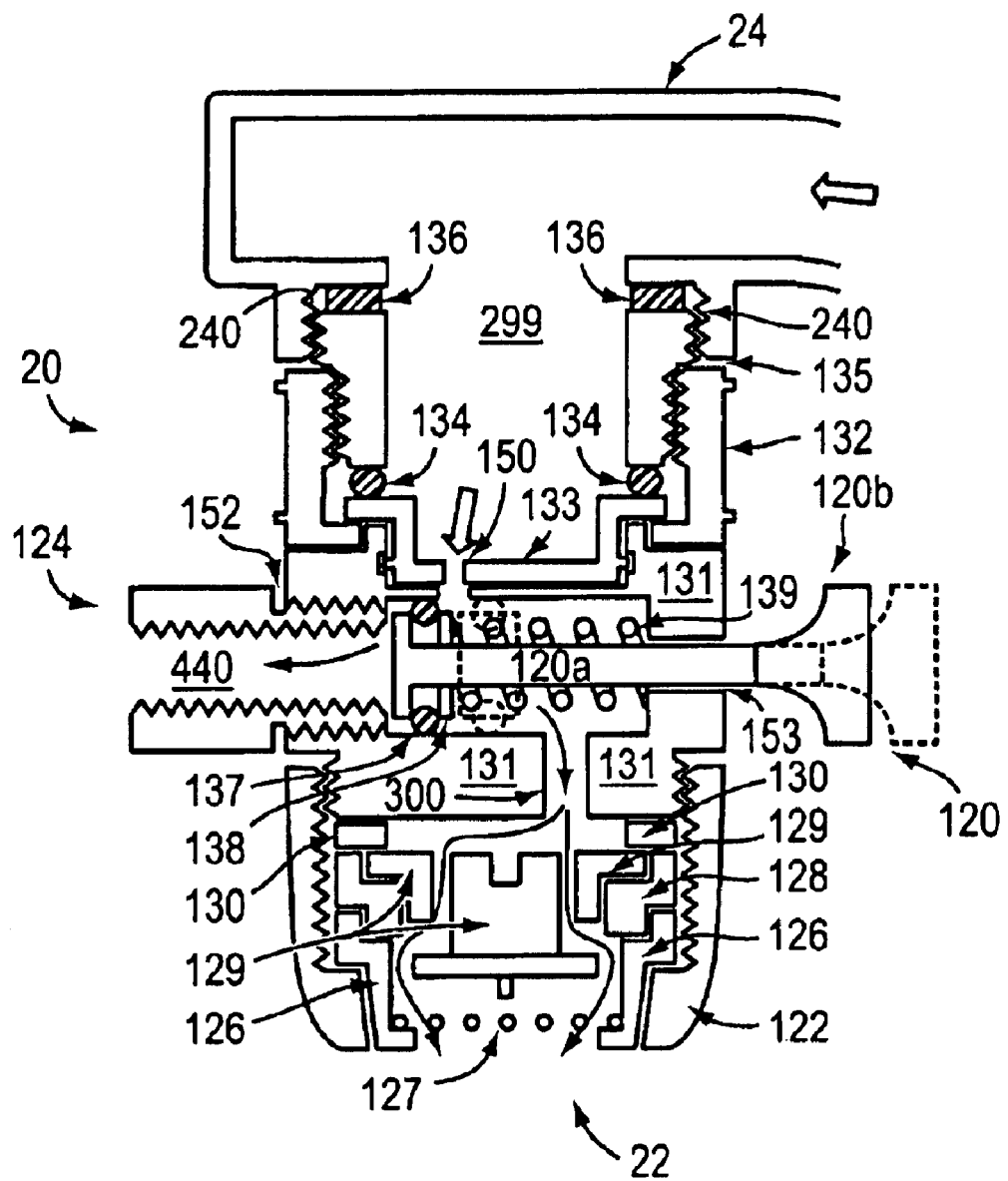
FIG. 3 is a cross-sectional view of the diverter valve assembly attached to a faucet.

Turning now to FIG. 3 further detail as to the configuration of the parts composing the diverter valve 20 and their assembly are shown. The operating of the valve stem assembly and how it can be used to divert water flow to different passages defined by the valve 20 is now described. The spring 138 biases the interior end of the valve stem 120 and O-ring 137 against the interior aperture of the outlet member 214, thus blocking water flow through the passage 440 defined in the interior of the outlet member 124. Water flow from faucet 24 moves through passage 299 defined by parts 132–136, through the aperture 150 defined in the passage definer 133, and further through passage 300 defined by parts 122 and 126–131 to exit at the valve's main orifice 122. Along this path, the water flow is rendered diffuse by the part 129 and screen 127 to form a desirable flow of water from the valve 20.

If the valve 120 is moved to the right in FIG. 3 so that the passage 300 is blocked by the washer 138 and O-ring 137, water from passage 299 of the valve 12 flows through the aperture 150 defined in the passage definer 133 and further through the passage 440 of the outlet member 124 to exit the valve and enter the coupling device 16. Thus, by pulling the valve stem 120 outwardly, a user can activate the apparatus 100 to deliver a cleansing spray jet 26 for oral hygiene.

Figure 4:
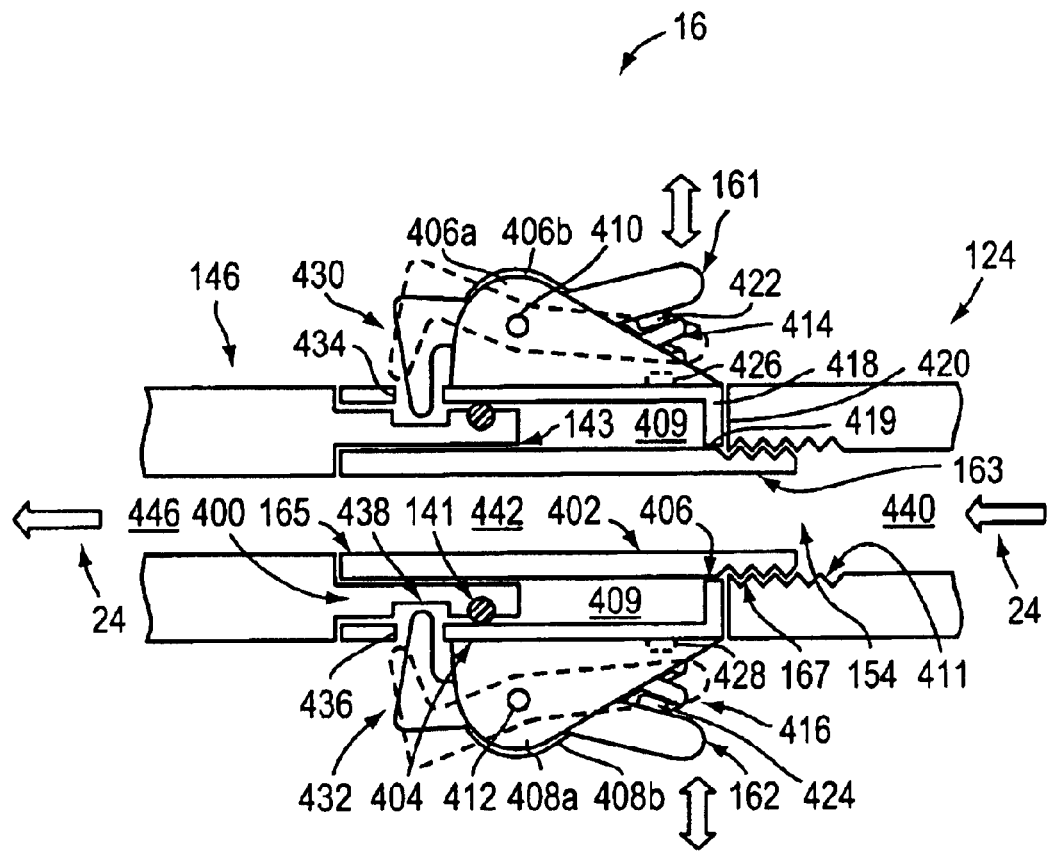
FIG. 4 is a cross-sectional view of a coupling device and portions of the valve and container to which the coupling device is attached.

FIG. 4 shows the coupling device 16 and parts of the diverter valve's outlet member 124 and the inlet member 146 of the container's cap portion 140. The coupling device 16 generally comprises an inner cylinder 402, outer cylinder 404, plates 406a, 406b, 408a, 408b, pivot pins 410, 412, and springs 414, 416. The inner cylinder 402 is positioned inside of outer cylinder 404 to define an annular space 409 between the cylinders for receiving the inlet member 146. The inner cylinder 402 defines an inner passage 442 through which water 24 flows. One end 418 of the outer cylinder 404 is substantially closed at its end but defines an aperture 419 through which extends the inner cylinder 402. The inner and outer cylinders 402, 404 can be joined by an adhesive or fused by heat treatment, for example, to form a joint 406 between the cylinders. The inlet end 167 of the inner cylinder 146 is threaded on its outer surface to join with corresponding threads 411 on the inner surface of the outlet member 124. Upon sufficient rotation of the coupling device 16 relative to the outlet member 124, the closed end 418 of the outer cylinder 404 meets with the end 420 of the outlet member 124 so that these elements are engaged together.

The outer surface of the outer cylinder 404 supports plates 406a, 406b, 408a, 408b. Plates 406a, 406b and 408a, 408b have edges joined to the outer surface of the outer cylinder 404 and are arranged in a spaced, opposing relationship to one another. Between such plates 406a, 406b, 408a, 408b extend respective pins 410, 412 that have ends support by such plates. The pins 410, 412 extend through respective levers 161, 162 so that the levers can pivot about such pins. The springs 414, 416 are situated on respective posts 422, 428 of the levers 161, 162 and respective posts 426, 428 extending from the outer surfaces of the cylinder 404. The springs 414, 416 bias respective levers 161, 162 so that the ends 430, 432 extend into respective holes 434, 436 defined in the outer cylinder's outer surface. As so positioned, the locking ends 430, 432 extend inside of the outer cylinder 404 within the annular groove 438 defined in the outer portion 400 of the inlet member 146. The ends 430, 432 thus lock the inlet member 146 to the coupling device 16. In this locked configuration, the O-ring 141 forms an annular ridge at the end of the inlet member 400 that engages with the inner surface of the outer cylinder 404 to form a liquid-tight seal and to align the inner cylinder's passage 442 with the passage 446 of the inlet member 146. Accordingly, the passage 442 defined by the inner surface of the inner cylinder 402 communicates with the passage 446 defined in the inlet member 146. In this configuration, water 24 can flow from the diverter valve's outlet member 124 through the coupling device 16 to the container's inlet member 146 via communicating passages 440, 442, 446 defined in these elements. To couple or decouple the inlet member 146 from the coupling device 16, a user can apply finger pressure to the levers 161, 162 to push them together against force exerted by the springs 414, 416 so that the ends 430, 432 move out of the annular groove 438, thus permitting the coupling device to be joined or separated from the inlet member 146 as desired. Releasing finger pressure on the levers 161, 162 allows the springs 414, 416 to force the locking ends 430, 432 into the annular groove 438 of the inlet member 146 to releasably lock the coupling device 16 to the inlet member 146.

Figure 5:
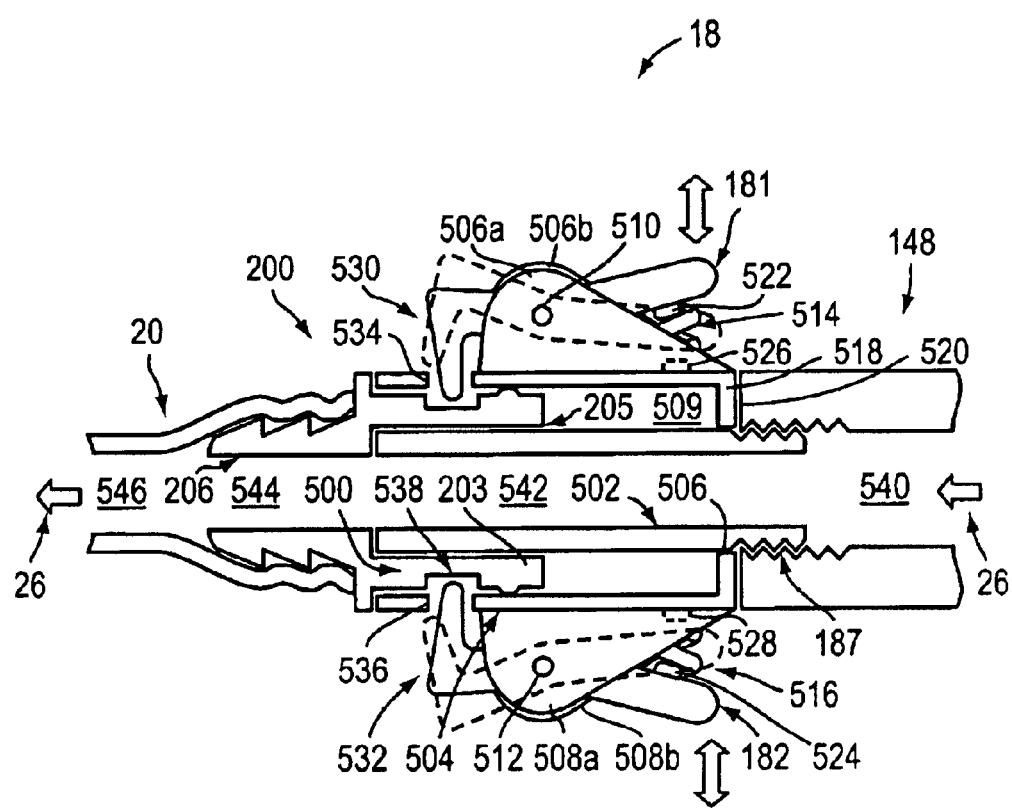
FIG. 5 is a cross-sectional view of a coupling device and portions of the diverter valve and hose to which the coupling device is attached.

In FIG. 5 the coupling device 18 is substantially the same as the coupling device 16, although it is joined to different parts of the apparatus 100. The coupling device 18 generally comprises an inner cylinder 502, outer cylinder 504, plates 506a, 506b, 508a, 508b, pivot pins 510, 512, and springs 514, 516. The inner cylinder 502 is positioned inside of outer cylinder 504, and extends through an aperture 506 in the closed end 518 thereof. The outer surface of the inner cylinder 502 is joined to the surfaces of the closed end 518 defining the aperture 506 with an adhesive or by fusing these elements together. The outer surface of the inner cylinder 502 and the inner surface of the outer cylinder 502 thus define an annular space 509 to receive inlet portion 500 of the coupler 200. The inlet end 187 of the coupling device 18 has threads that are joined with those of the outlet member 148 by rotating the coupling device relative to the outlet member until closed end 518 meets with end surface 520 of the outlet member. Plates 506a, 506b, and 508a, 508b are attached to the outer surface of the outer cylinder 504 on opposite sides thereof. The plates 506a, 506b and 508a, 508b are attached to the outer cylinder 504 in a spaced opposing relationship. Levers 181, 182 are positioned between respective plates 506a, 506b and 508a, 508b, and are pivotally supported by respective pivot pins 510, 512 that extend through the opposing plates 506a, 506b and 508a, 508b and have ends fixed thereto. The springs 514, 516 have ends fixed on respective posts 522, 524 of levers 181, 182 and opposite ends fixed on respective posts 526, 528 extending from the outer surface of the outer cylinder 504. The levers 181, 182 are thus biased so that the locking ends 530, 532 of the levers 181, 182 are positioned in holes 534, 536 defined on opposite sides of the outer cylinder 504. Accordingly, the locking ends 530, 532 extend into the interior space of the outer cylinder 504 where they are situated in annular groove 538 defined in the inlet portion 500 of the coupler 200. The inlet portion 500 of the coupler 200 can thus be secured to the coupling device 16. In this position, the annular ridge 203 of the coupler 200 engages with the inner surface of the outer cylinder 504 to align the inner so that the inner surface of the inner cylinder 502 and inner surface of coupler 200 defining respective passages 542, 544 are aligned to permit passage of the liquid mixture 26. The liquid mixture 26 can thus travel through passages 540, 542, 544, 546 defined in the outlet member 148, the coupling device 18, the coupler 200, and the hose 20.

If it is desired to decouple or insert the coupler 200 into the coupling device 18, the user applies finger pressure to squeeze levers 181, 182 against the force applied by springs 514, 516 toward the outer surface of the outer cylinder 404. This squeezing action causes the levers 530, 532 to pivot about respective pins 510, 512 so that the locking ends 530, 532 retract from the annular groove 538 of the coupler 200. The levers 181, 182 are thus positioned as shown in broken line in FIG. 5. As so positioned, the coupler 200 can be freely inserted into or extracted from the coupling device 18. Releasing finger pressure on the levers 181, 182 allows the springs 514, 516 to force the locking ends 530, 532 into the annular groove 538 of the coupler 200 to releasably lock the coupling device 18 to the coupler.

Figure 6:
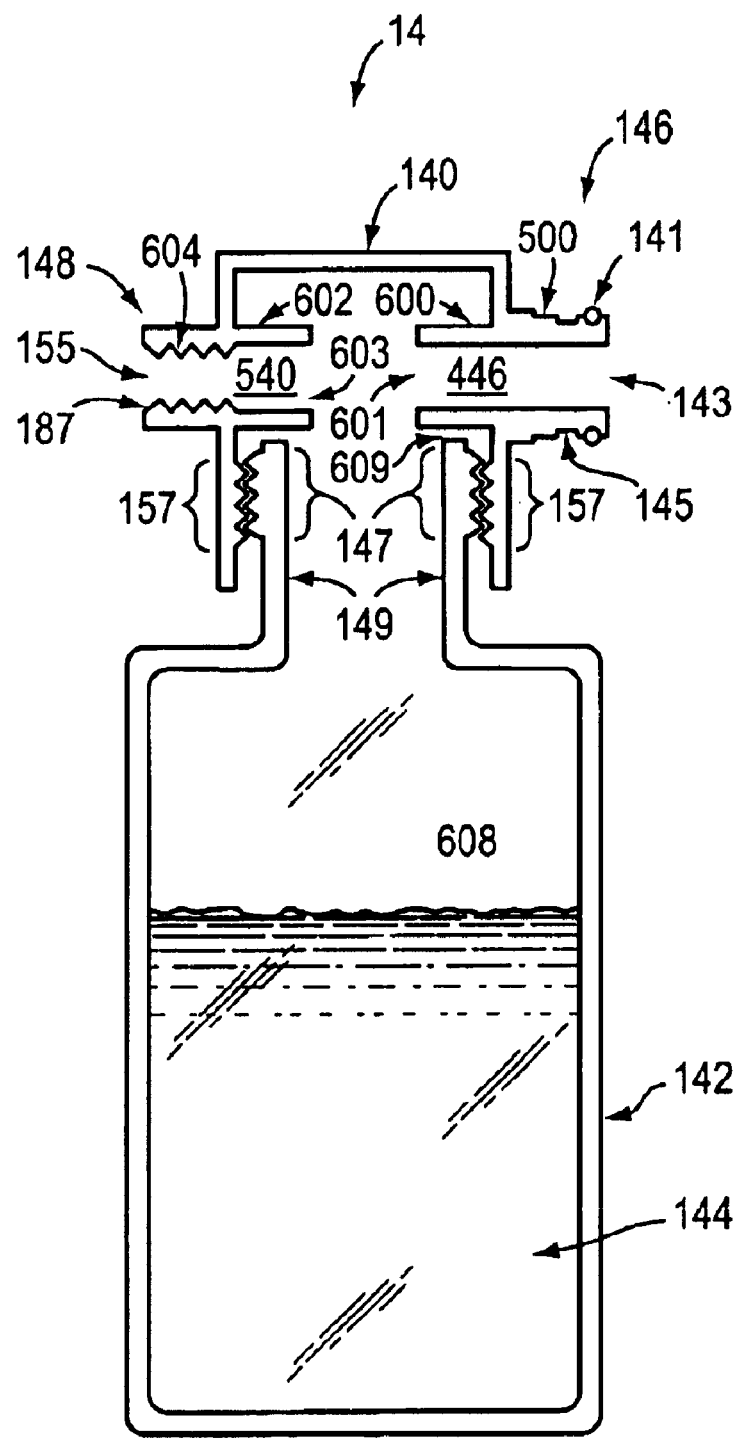
FIG. 6 is a cross-sectional view of a container used in the oral hygiene apparatus to hold oral hygiene substance.

FIG. 6 shows the cap portion 140 of the container 14 joined to the containment portion 142. The cap portion 140 can be cylindrical in shape, for example. The cap portion 140 can be removed from the containment portion 150 by twisting the cap portion relative to the containment portion 142. Threads 157 defined in the inner surface of the cap portion 140 move in contact with intermeshing threads 149 defined in the neck 147 of the container 14 until the threads clear one another so that the containment portion 142 can be separated from the cap portion 142. Oral hygiene substance 144 can then be poured or transferred into container 14 via aperture 609 in the neck 147. The cap portion 140 is then twisted onto the containment portion 142 to enclose substances 144 therein.

The cap portion 140 comprises inlet member 146 and outlet member 148. The components of the member 146 on its outer portion 500 have been previously described. These components comprises the annular groove 146 defined in the outer surface of the inlet member 146, the O-ring 141, the orifice 143 defined at the end of the outer portion 500, and the passage 446 defined internally in the inlet member 146. The inlet member 146 also comprises an interior portion 600 that defines an aperture 601 of the passage 446 that communicates with the interior space 608 of the container 14. Water 24 from the valve 20 and coupling device 16 can thus travel to the interior space 608 of the container 14. Inside of the container 14 the water 24 mixes with oral hygiene substance 144 to form liquid mixture 26. The outlet member 148 has an interior portion 602 that defines aperture 603 permitting the passage 540 defined by the outlet member to communicate with interior space 608 of the container 14. The flow of water 24 from the inlet member 146 into the container 14 eventually fills the container so that the liquid mixture 26 resulting from mixing of the water 24 and oral hygiene substance 144 passes through the orifice 603 through the passage 540 defined in the outlet member 148 to exit the container at orifice 155 of the outlet member.

Figure 7:
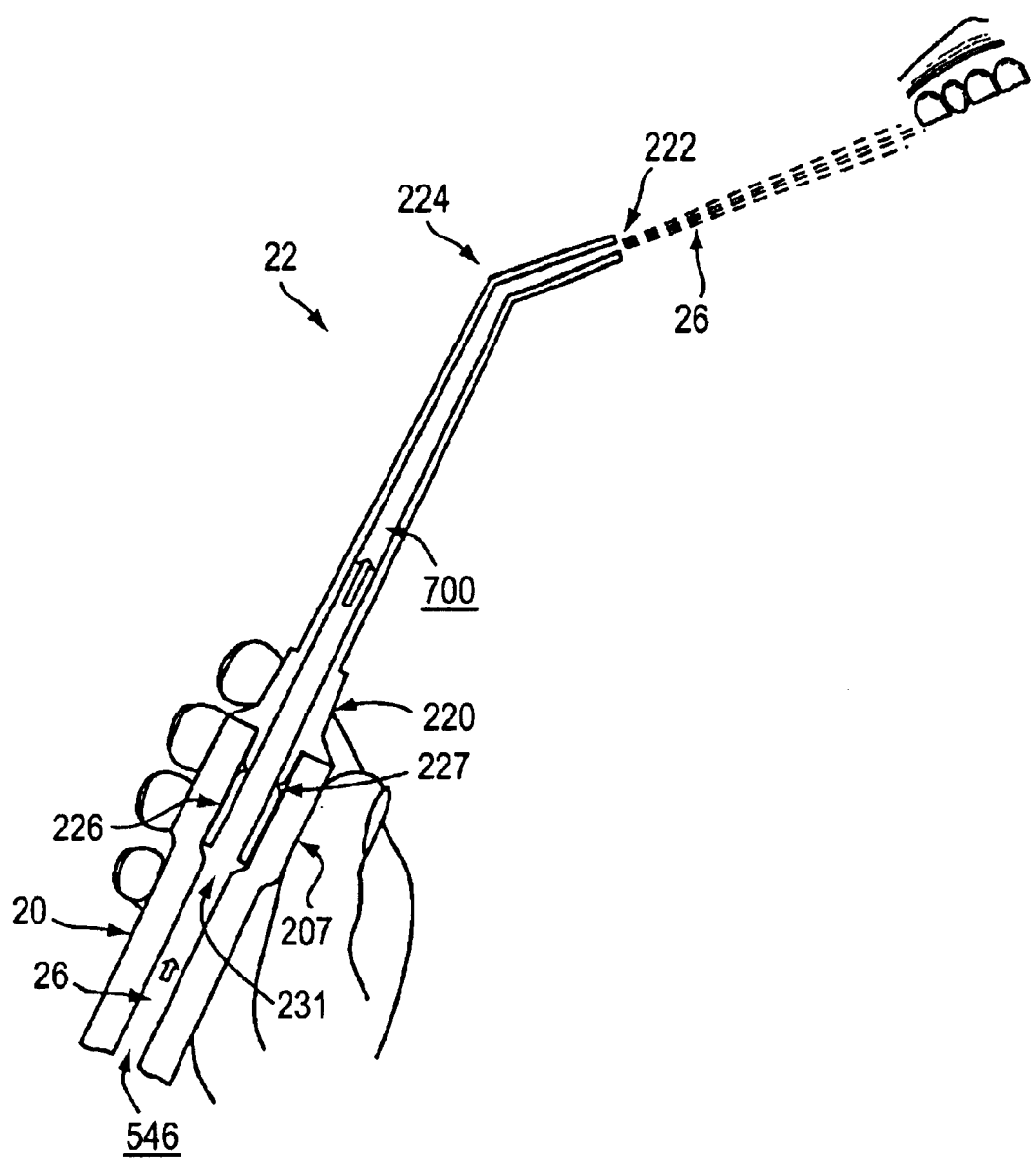
FIG. 7 is a cross-sectional view of a jet tip and a portion of a hose coupled thereto.

FIG. 7 shows the jet tip 22 and a portion of the hose 20 coupled thereto. The hose end 207 is stretched open and slid over the base end 226 of the jet tip 22 to abut with the grip 220 that acts as a stop for the hose. Due to its resilience, the hose 20 relaxes in the groove 227 to enhance friction between the jet tip 22 and the hose 20 to prevent their inadvertent separation. The passage 546 defined by the hose 20 communicates through the aperture 231 with the passage 700 defined in the jet tip 22 to permit the liquid mixture 26 to pass through the jet tip 22 from aperture 222 in a spray jet 26. A user of the apparatus 10 grips the jet tip 22 with a hand and directs the spray jet 26 to the user's teeth and/or gums. If the substance 144 in the liquid mixture 26 is a mouthwash, the spray jet 26 acts on the teeth and/or gums to destroy microbes and freshen the breath. If the substance 144 in the liquid mixture 144 is fluoride or other oral treatment, it is applied to the user's teeth by the jet tip 22 and is absorbed by the teeth for their strengthening. If the substance 144 is sodium bicarbonate or other soft material, the spray jet 26 directs such material against the teeth and gums to clean away plaque, tartar or other debris. The material in the spray jet 26 is directed against the teeth and gums with sufficient velocity to thoroughly clean them, yet with insufficient velocity to abrade or otherwise damage the teeth or soft tissues of the mouth.

The many features and advantages of the present invention are apparent from the detailed specification and thus, it is intended by the appended claims to cover all such features and advantages of the described apparatuses which follow in the true spirit and scope of the invention. Further, since numerous modifications and changes will readily occur to those of ordinary skill in the art, it is not desired to limit the invention to the exact construction and operation illustrated and described. Accordingly, all suitable modifications and equivalents may be resorted to as falling within the scope of the invention.

What is claimed is:

1. An oral hygiene apparatus for use with a faucet providing a flow of water and for use with an oral hygiene substance, the apparatus comprising:

a valve adapted to fit to the faucet to receive a flow of water therefrom, the valve controllable to selectively provide the water flow through a first faucet orifice and a second auxiliary orifice;

a container holding the oral hygiene substance;

a first coupling device releasably locking the valve in communication with the container so that the water flow travels from the valve at its second orifice to the container, the water mixing with the oral hygiene substance in the container to produce a liquid mixture;

a hose having first and second ends;

a second coupling device releasably locking the container in communication with the hose, the second coupling device receiving a flow of the liquid mixture from the container and supplying the liquid mixture flow to the first end of the hose; and a jet tip coupled to the second end of the hose, the jet tip receiving the liquid mixture flow and generating a spray jet with the liquid mixture flow for use in oral hygiene;

wherein at least one of said first and second coupling devices comprises opposing spring-loaded levers operable to selectively couple respective passages of first and second elements in communication with one another, each said spring-loaded lever pivotally mounted to an outer surface of said coupling device at a fulcrum positioned between a locking end and a releasing end of said lever, said lever mounted along a longitudinal direction of said coupling device such that said locking end extends towards an outer surface of said coupling device and is spring-biased to releasably lock into a groove on said first or second element.

2. An apparatus as claimed in claim 1 wherein the container comprises a cap portion and a containment portion, the cap portion removably securable to the containment portion to enclose the oral hygiene substance, the first and second coupling devices coupling to the cap portion so that the containment portion can be freely separated from the cap portion to load the container with the oral hygiene substance with the cap portion remaining attached to the valve and hose.

3. An apparatus as claimed in claim 1 further comprising:
an additional container enclosing a different oral hygiene substance than the first container, the coupling devices releasable from the first container and recoupled to the additional container to change the oral hygiene substance used to produce the liquid mixture.

4. An apparatus as claimed in claim 1 wherein the first coupling device comprises opposing spring-loaded levers operable to selectively couple the valve and container in communication with one another and to release the valve and container from communication with one another.

5. An apparatus as claimed in claim 1 wherein the first coupling device has a threaded end that can be screwed into an outlet member defining the second auxiliary orifice of the valve to secure the first coupling device and valve together.

6. An apparatus as claimed in claim 5 wherein the first coupling device has opposing spring-loaded levers for locking the first coupling device in communication with an inlet member of the container.

7. An apparatus as claimed in claim 1 wherein the second coupling device has a threaded end that can be screwed into an outlet member of the container to couple the second coupling device and the container together.

8. An apparatus as claimed in claim 7 wherein the second coupling device has opposing spring-loaded levers for locking the second coupling device in communication with a coupler of the hose.

9. An apparatus as claimed in claim 1 wherein the second coupling device comprises opposing spring-loaded levers operable to selectively couple the container and hose in communication with one another and to release the container and hose from communication with one another.

10. An apparatus as claimed in claim 1 wherein the jet tip defines a passage with a relatively wide aperture at its base end tapering to a relatively narrow aperture at its opposite tip end, the base end with the relatively wide aperture coupled in communication with the hose to receive the liquid mixture therefrom, the liquid mixture flowing into the base end and through the jet tip's passage and emitted from the relatively narrow aperture at the opposite end of the jet tip in a relatively high-velocity spray jet as compared to the velocity of the liquid mixture flow into the base end of the jet tip.

11. A oral hygiene apparatus for use with a faucet providing a flow of water and a oral hygiene substance, the apparatus comprising:
valve means adapted to fit to the faucet to receive a flow of water therefrom, for selectively providing the water flow through a first faucet orifice and a second auxiliary orifice;
container means for holding the oral hygiene substance;
first coupling device means for releasably locking the valve means in communication with the container means so that the water flow travels from the valve means at its second orifice to the container means, the water mixing with the oral hygiene substance in the container means to produce a liquid mixture;
hose means having first and second ends, for guiding the liquid mixture from the container means;
second coupling device means for releasably locking the container means in communication with the hose means, the second coupling device means receiving a flow of the liquid mixture from the container means and supplying the liquid mixture flow to the first end of the hose means; and
jet tip means coupled to the second end of the hose, the jet tip means for receiving the liquid mixture flow and for generating a spray jet with the liquid mixture flow for use in oral hygiene,
wherein at least one of said first and second coupling device means comprises opposing spring-loaded levers operable to selectively couple respective passages of first and second elements in communication with one another, each said spring-loaded lever pivotally mounted to an outer surface of said coupling device means at a fulcrum positioned between a locking end and a releasing end of said lever, said lever mounted along a longitudinal direction of said coupling device means such that said locking end extends towards an outer surface of said coupling device means and is spring-biased to releasably lock into a groove on said first or second element.

12. An apparatus as claimed in claim 11 wherein the container means comprises a cap portion and a containment portion, the cap portion removably securable to the containment portion to enclose the oral hygiene substance, the first and second coupling device means coupling to the cap portion so that the containment portion can be freely separated from the cap portion to load the container means with the oral hygiene substance with the cap portion remaining attached to the valve means and hose means.

13. An apparatus as claimed in claim 11 further comprising:
an additional container means for enclosing a different oral hygiene substance than the first container means, the coupling device means releasable from the first container means and recoupled to the additional container means to change the oral hygiene substance used to produce the liquid mixture.

14. An apparatus as claimed in claim 11 wherein the first coupling device means comprises opposing spring-loaded levers operable to selectively couple the valve means and container means in communication with one another and to release the valve means and container means from communication with one another.

15. An apparatus as claimed in claim 11 wherein the first coupling device means has a threaded end that can be screwed into an outlet member defining the second auxiliary orifice of the valve means to secure the first coupling device and valve means together.

16. An apparatus as claimed in claim 15 wherein the first coupling device means has opposing spring-loaded levers for locking the first coupling device means in communication with an inlet member of the container means.

17. An apparatus as claimed in claim 11 wherein the second coupling device means has a threaded end that can be screwed into an outlet member of the container means to couple the second coupling device means and the container means together.

18. An apparatus as claimed in claim 17 wherein the second coupling device means has opposing spring-loaded levers for locking the second coupling device means in communication with a coupler of the hose means.

19. An apparatus as claimed in claim 11 wherein the second coupling device means comprises opposing spring-loaded levers operable to selectively couple the container means and hose means in communication with one another and to release the container means and hose means from communication with one another.

20. An apparatus as claimed in claim 11 wherein the jet tip means defines a passage with a relatively wide aperture at its base end tapering to a relatively narrow aperture at its opposite tip end, the base end with the relatively wide aperture coupled in communication with the hose means to receive the liquid mixture therefrom, the liquid mixture flowing into the base end and through the jet tip means' passage and emitted from the relatively narrow aperture at the opposite end of the jet tip in a relatively high-velocity spray jet as compared to the velocity of the liquid mixture flow into the base end of the jet tip means.

\* \* \* \* \*